(12) United States Patent
Griffin et al.

(10) Patent No.: US 7,473,228 B2
(45) Date of Patent: Jan. 6, 2009

(54) SYSTEM AND METHOD FOR MONITORING A RESPIRATION RATE OF AN OCCUPANT OF A PREDETERMINED VOLUME

(75) Inventors: Dennis P. Griffin, Noblesville, IN (US); William W. Fultz, Carmel, IN (US)

(73) Assignee: Delphi Technologies, Inc., Troy, MI (US)

( * ) Notice: Subject to any disclaimer, the term of this patent is extended or adjusted under 35 U.S.C. 154(b) by 614 days.

(21) Appl. No.: 10/887,502

(22) Filed: Jul. 8, 2004

(65) Prior Publication Data
US 2006/0009703 A1 Jan. 12, 2006

(51) Int. Cl.
*A61B 5/02* (2006.01)
(52) U.S. Cl. .................. 600/529; 600/534; 600/538
(58) Field of Classification Search ........... None
See application file for complete search history.

(56) References Cited

U.S. PATENT DOCUMENTS

| 4,197,856 A | 4/1980 | Norethrop et al. |
|---|---|---|
| 4,422,458 A | 12/1983 | Kravath |
| 5,361,070 A | 11/1994 | McEwan |
| 5,386,833 A | 2/1995 | Uhen |
| 5,638,824 A | 6/1997 | Summers |
| 5,966,090 A | 10/1999 | McEwan |
| 6,062,216 A | 5/2000 | Corn |
| 2001/0042977 A1 | 11/2001 | Breed et al. |

OTHER PUBLICATIONS

European Search Report dated Oct. 5, 2005.

*Primary Examiner*—Robert L Nasser
(74) *Attorney, Agent, or Firm*—Jimmy L. Funke (57) ABSTRACT

An ultrasonic sensing system includes an ultrasonic transmitter, an ultrasonic receiver, a processor and a memory subsystem. The transmitter is positioned to transmit an ultrasonic signal into a predetermined volume. The receiver is positioned to receive a composite signal from the predetermined volume. The processor is coupled to the transmitter, the receiver and the memory subsystem. The memory subsystem stores code that when executed by the processor instructs the processor to perform a number of steps to determine whether an occupant is present in the predetermined volume and whether the detected occupant has a respiration rate.

30 Claims, 5 Drawing Sheets

SYSTEM AND METHOD FOR MONITORING A RESPIRATION RATE OF AN OCCUPANT OF A PREDETERMINED VOLUME

TECHNICAL FIELD

The present invention is generally directed to a system and method for monitoring a respiration rate of an occupant of a predetermined volume and, more specifically, an ultrasonic sensing system for monitoring a respiration rate of an occupant of a predetermined volume.

BACKGROUND OF THE INVENTION

Various systems have been designed to detect and classify occupants of a predetermined volume. For example, detection and classification systems have been utilized in the field of security to detect intruders and in the field of safety to determine whether, for example, a human being is trapped within a predetermined volume. Detection and classification systems have also been utilized in personal health and medical applications. A variety of systems have been proposed and/or developed for the purposes of monitoring a predetermined volume, such as a room of a building, a vehicle interior and/or other defined volumes. One such system has implemented ultrasonic technology to determine the presence of a human being within a predetermined volume. In general, such ultrasonic systems implement acoustic wave signals with frequencies above the normal range of human hearing. Many such systems have transmitted ultrasonic signals in a pulse mode and analyzed a returning reflected signal using a time-of-flight concept. Other ultrasonic systems have employed continuous transmission and have analyzed returning reflected signals for a Doppler shift.

While many known systems are successful in certain applications, within certain limitations, in detecting a moving occupant and generating an alert that is interpreted as detection of a living occupant, such systems have generally been hampered by their inability to deal with problems in acoustical impedance of various transmission media. Generally, such systems have also had difficulty in dealing with wave interference caused in received signals, which are composite signals that include portions of both a transmitted and reflected acoustic wave. As such, prior art systems have generally been limited to the detection of gross body movements and, as a result, have not been sufficiently sensitive to reliably detect small movements characteristic of a respiration of a human being, which involves only relatively small body movements.

What is needed is a technique that is capable of accurately monitoring a respiration rate of an occupant of a predetermined volume. It would also be desirable if the technique had the ability to acquire, lock and continually track the respiration rate of the occupant, especially when other body movements are present.

SUMMARY OF THE INVENTION

According to the present invention, an ultrasonic sensing system includes an ultrasonic transmitter, an ultrasonic receiver, a processor and a memory subsystem. The transmitter is positioned to transmit an ultrasonic signal into a predetermined volume. The receiver is positioned to receive a composite signal from the predetermined volume. The processor is coupled to the transmitter, the receiver and the memory subsystem. The memory subsystem stores code that when executed by the processor instructs the processor to perform a number of steps. One step includes analyzing frequency component amplitudes of a received ultrasonic signal to determine a frequency content of the received ultrasonic signal, which is a composite signal that provides an indication of a respiration rate of an occupant present within a predetermined volume. Another step includes determining whether a current peak respiration rate is the same as a previous peak respiration rate. Yet another step involves incrementing a current peak respiration rate counter, when the current peak respiration rate is the same as the previous peak respiration rate. Still another step includes decrementing a previous peak respiration rate counter, when the current peak respiration rate is not the same as the previous peak respiration rate and an amplitude of the current peak respiration rate is a predetermined amount greater than an amplitude of the previous peak respiration rate.

According to another aspect of the present invention, the previous peak respiration rate counter is also decremented when the current peak respiration rate is not the same as the previous peak respiration rate and the current peak respiration rate corresponds to a respiration rate that is adjacent to the previous peak respiration rate. According to a different embodiment of the present invention, the current peak respiration rate counter and the previous peak respiration rate counter are not altered unless the frequency component amplitudes of the received ultrasonic signal indicate a detected respiration rate and the presence of the occupant in the predetermined volume. According to a different aspect of the present invention, the current peak respiration rate counter is only incremented if a value of the current peak respiration rate counter is less than a predetermined maximum counter value and the current peak respiration rate is the same as the previous peak respiration rate. According to a different embodiment of the present invention, the previous peak respiration rate counter is only decremented if a value of the previous peak respiration rate counter is more than a predetermined minimum counter value.

According to yet another aspect of the present invention, the memory subsystem stores additional code for instructing the processor to perform a number of additional steps. One step includes determining whether amplitudes associated with respiration rates adjacent the current peak respiration rate are within a predetermined value of an amplitude of the current peak respiration rate. Another step includes incrementing an adjacent lower respiration rate counter when the amplitude of the adjacent lower respiration rate is within the predetermined value of the amplitude of the current peak respiration rate. Yet another step includes incrementing an adjacent upper respiration rate counter when the amplitude of the adjacent upper respiration rate is within the predetermined value of the amplitude of the current peak respiration rate. Still another step includes determining an average respiration rate based on the values of the adjacent lower respiration rate counter, the adjacent upper respiration rate counter and a current peak respiration rate counter.

According to another embodiment of the present invention, the adjacent lower respiration rate counter is only incremented if a value of the adjacent lower respiration rate counter is less than a predetermined maximum counter value. Similarly, the adjacent upper respiration rate counter is only incremented if a value of the adjacent upper respiration rate counter is less than the predetermined maximum counter value. According to yet another aspect of the present invention, the counters are cleared when the frequency component amplitudes of the received ultrasonic signal indicate that there are no occupants present in the predetermined volume or the occupant does not have a respiration rate. According to various embodiments of the present invention, the frequency content is between 0 and 300 Hertz.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

According to the present invention, an ultrasonic sensing system is disclosed herein that is programmed to acquire, lock and track a respiration rate of an individual located within a predetermined volume, such as an interior of a vehicle, even when other body movements are present within the predetermined volume. This feature enables the ultrasonic sensing system to monitor the respiration rate of an individual and combine this data with other available sensor data, for example, temperature and humidity, to identify possible at-risk situations in, for example, an automotive passenger compartment or other enclosed area.

Various ultrasonic sensing systems have been proposed or implemented to monitor an occupant of a predetermined volume. For example, U.S. Pat. No. 6,932,769, entitled ULTRASONIC OCCUPANT DETECTION AND CLASSIFICATION SYSTEM, which is commonly assigned to the assignee of the present invention and which is incorporated herein by reference in its entirety, incorporates an ultrasonic transmitter and receiver that operates in near continuous mode and utilizes the properties of acoustic impedance and acoustic interference to perform occupant sensing functions.

In the case of a vehicle interior application, a beam angle of forty to fifty degrees allows a broad area of coverage without degradation of the sensitivity of the sensor. The reflected signals from a target are detected by the ultrasonic receiver and are passed through a signal processing circuit that detects changes in the signals that result from movement and/or dynamic changes in the target field of view. The changes in a target's ultrasonic reflections combine to create frequency amplitude and phase changes in a composite signal at the receiver. An ultrasonic sensing system so designed is capable of detecting even slight movement, such as respiration, and other movements of a human being. In general, the ultrasonic sensing system extracts signal components from a received composite signal by demodulating and filtering the composite signal to derive frequency data that is analyzed to classify an occupant of a predetermined volume, according to predetermined stored frequency data characteristics of live occupant movement. In general, to determine a respiration rate of an occupant within a vehicle, a received signal is filtered to provide signals within a frequency range of 0 to 3 Hertz for further analysis. Signals within the frequency range 0 to 3 Hertz are digitally filtered and the filtered signals are assigned to frequency bands, for example, a range from 0 to 3 Hertz may be divided into fifteen bands with each band having 0.2 Hertz bandwidth.

A similar frequency domain analysis is utilized to detect, filter and segregate components of a received signal into the various other frequency components of movement, for example, within a range of 3 to 300 Hertz. According to the present invention, when a respiration rate is acquired, the system locks onto corresponding frequency data and tracks any subsequent changes in the respiration rate. In doing so, the ultrasonic sensing system primarily relies on the periodicity of respiration to extract respiration data from other movement data detected by the system.

Figure 1:
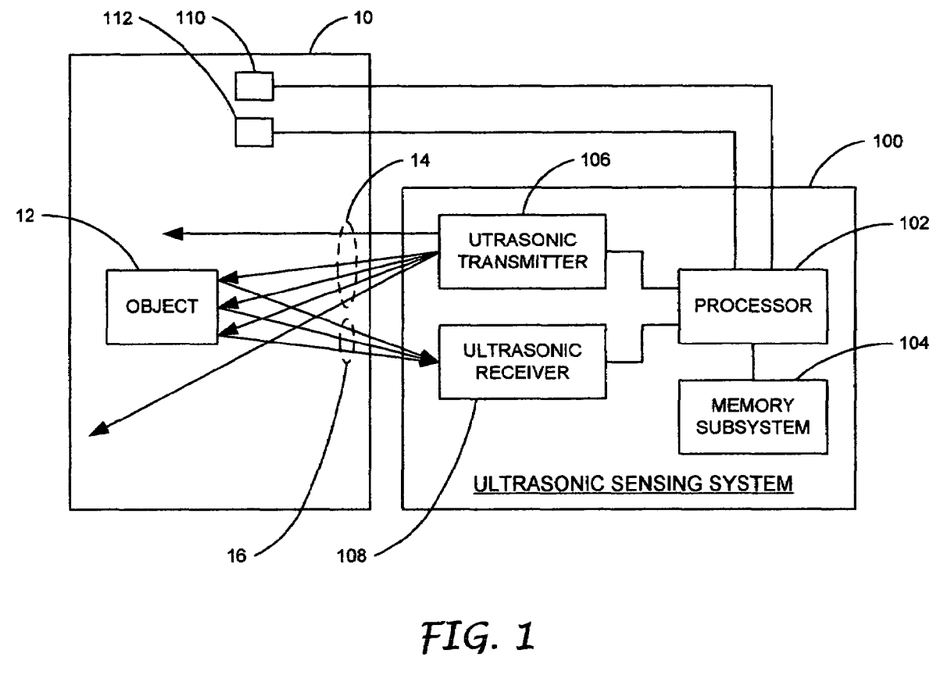
FIG. 1 is a block diagram of an ultrasonic sensing system that is utilized to monitor a respiration rate of an occupant of a predetermined volume.

With reference to FIG. 1, a block diagram of an ultrasonic sensing system constructed according to one embodiment of the present invention is depicted. As is shown, the ultrasonic sensing system 100 includes an ultrasonic transmitter 106 and an ultrasonic receiver 108, each coupled to a processor 102. The processor 102 is also coupled to a memory subsystem 104 and to a remote humidity sensor 112 and a remote temperature sensor 110, which are both located within a predetermined volume 10, e.g., a passenger compartment of an automobile. The ultrasonic transmitter 106 is positioned to provide an ultrasonic signal into the predetermined volume 10 and the ultrasonic receiver 108 is positioned to receive signals reflected from an object 12 located within the predetermined volume 10. As previously mentioned, the signals received by the ultrasonic receiver 108 are composite signals, which may include components of both a reflected signal and a transmitted signal. As used herein, the term processor may include a general purpose processor, a microcontroller (i.e., an execution unit with memory, etc., integrated within a single integrated circuit), an application specific integrated circuit (ASIC), a programmable logic device (PLD) or a digital signal processor (DSP).

Figure 2A:
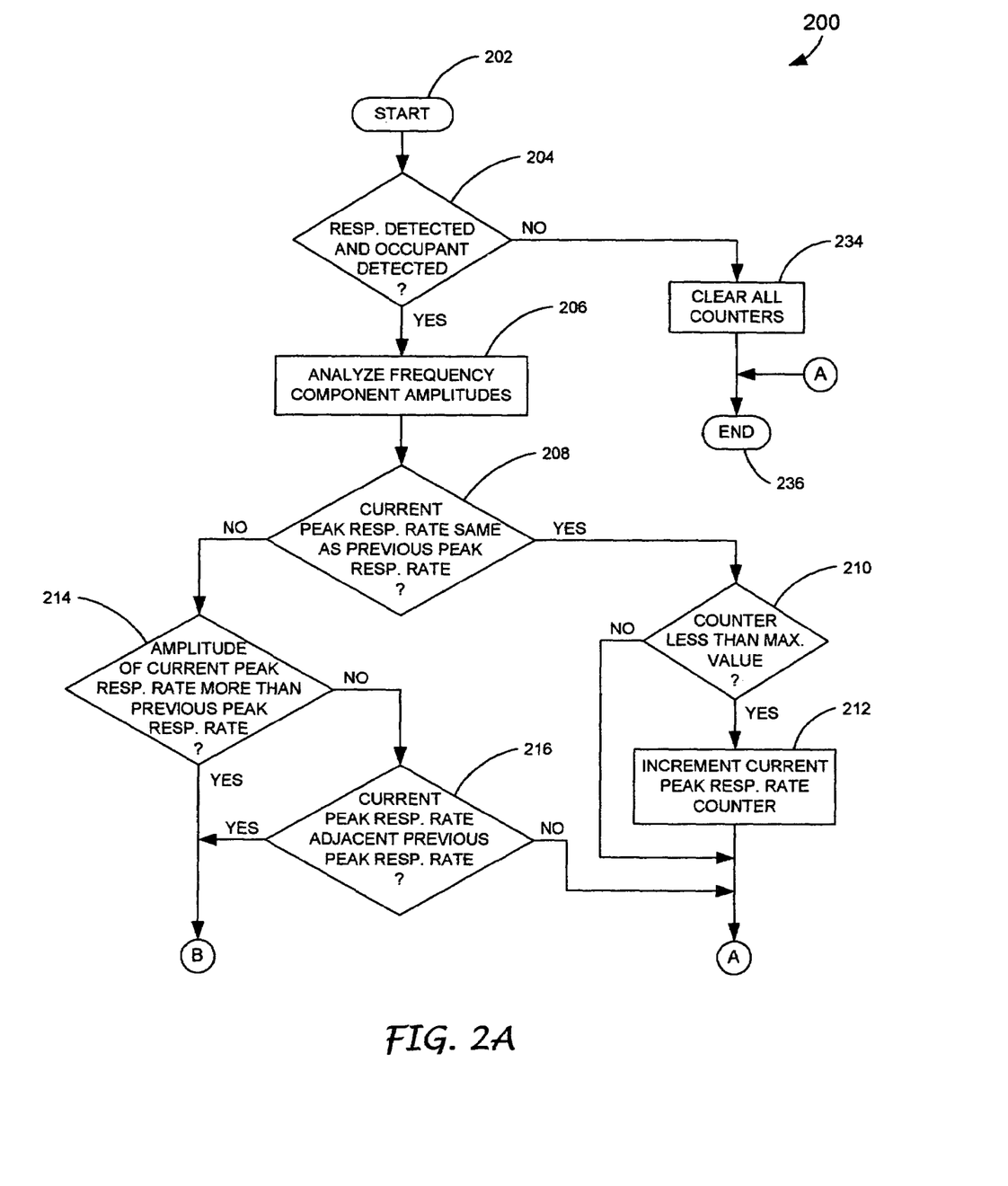
FIGS. 2A-2B are flow charts of an exemplary routine for acquiring, locking and tracking a respiration of an individual within a predetermined volume.
Figure 2B:
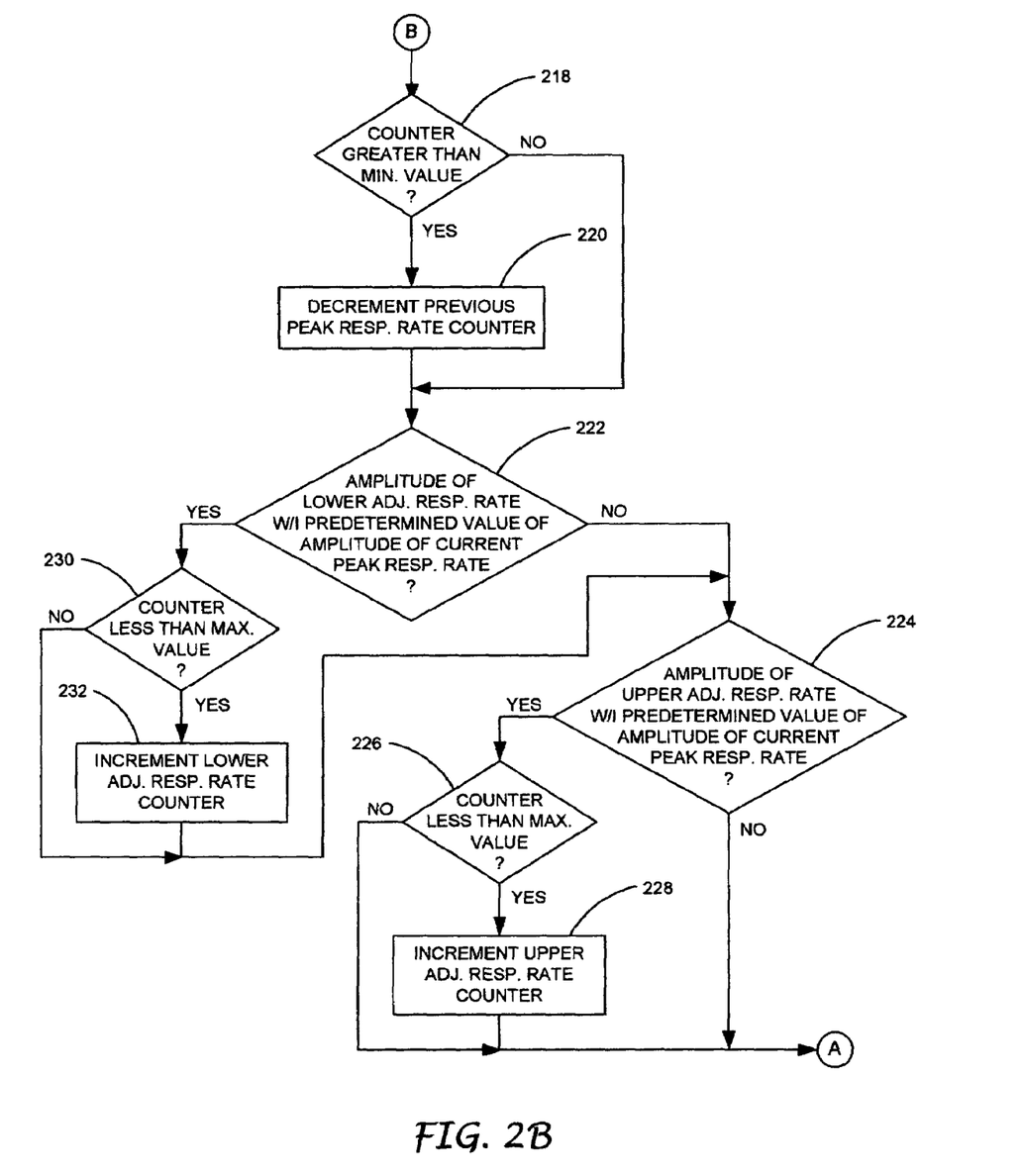

With reference to FIGS. 2A and 2B, a routine 200 is depicted, which allows the ultrasonic sensing system 100 to acquire, lock and track a respiration of an occupant, located within a predetermined volume. The routine 200 is initiated in step 202, at which point control transfers to decision step 204, where the processor 102 implementing the routine 200 determines if both respiration and an occupant are detected. As is disclosed in U.S. Pat. No. 6,932,769, respiration is detected when a signal between 0 and 3 Hertz is detected for a predetermined number of successive samples and when body movement is detected, i.e., a signal between 3 and 300 Hertz, is detected for a predetermined number of successive samples. When both respiration and an occupant are detected in step 204, control transfers to step 206, where the processor 102 analyses the frequency component amplitudes of a received composite signal, before transferring control to decision step 208.

In step 208, the processor 102 determines whether a current peak respiration rate is the same as a previous peak respiration rate. It should be appreciated that when the routine 200 is executed at power-up, there is no previous peak respiration rate. As such, on initial power-up, control transfers from step 208 to decision step 214. In step 214, the processor 102 determines whether the amplitude of the current peak respiration rate is more than the previous peak respiration rate. If so, control transfers to step 218. Otherwise, control transfers to decision step 216, where the processor 102 determines whether the current peak respiration rate is adjacent the previous peak respiration rate. If so, control transfers to decision step 218. Otherwise, control transfers from step 216 to step 236, where the routine 200 terminates.

In step 208, when the current peak respiration rate is the same as the previous peak respiration rate, control transfers to step 210. In step 210, the processor 102 determines whether the current peak respiration rate counter is less than a maximum value. If so, control transfers to step 212, where the current peak respiration rate counter is incremented, before transferring control to step 236, where the routine 200 terminates. Otherwise, if the current peak respiration rate counter is equal to its maximum value in step 210, control transfers directly to step 236.

When the current peak respiration rate is adjacent the previous peak respiration rate in step 216, control transfers to step 218 and then to step 220, where the previous peak respiration rate counter is decremented, when the current peak respiration rate counter is greater than an assigned minimum value. When the previous peak respiration rate counter is not greater than the assigned minimum value in step 218, control transfers to decision step 222.

In step 222, the processor 102 determines whether the amplitude of a lower adjacent respiration rate is within a predetermined value of an amplitude of a current peak respiration rate. If so, control transfers from step 222 to decision step 230, where the processor 102 determines whether the lower adjacent respiration rate counter is less than a maximum value. If so, control transfers to step 232, where the adjacent lower respiration rate counter is incremented, and then to decision step 224. Otherwise, control transfers from step 230 directly to step 224. When the amplitude of the lower adjacent respiration rate is not within a predetermined value of the amplitude of the current peak respiration rate in step 222, control transfers to step 224.

In step 224, the processor 102 determines whether the amplitude of the upper adjacent respiration rate is within a predetermined value of the amplitude of the current peak respiration rate. If so, control transfers from step 224 to decision step 226, where the processor 102 determines whether the upper adjacent respiration rate counter is less than a maximum value. If so, control transfers to step 228, where the upper adjacent respiration rate counter is incremented, before transferring control to step 236. If the upper adjacent respiration rate counter is not less than a maximum value in step 226, control transfers directly to step 236. In step 224, when the amplitude of the upper adjacent respiration rate is not within a predetermined value of the amplitude of the current peak respiration rate, control transfers directly to step 236, where the routine 200 terminates.

Returning to step 204, if the processor 102 does not detect respiration and an occupant, control transfers from step 204 to step 234, where all counters are cleared before control transfers to step 236, where the routine 200 terminates.

Exemplary code for implementing the routine 200 of FIGS. 2A-2B is set forth below:

```
if ((DetStat & 0xFF00) = = 0x1100)      {
    if (maxindx = = lstrindx)       {
        avgrespn = maxindx+1 < < 1; avgrctr = 1;
        if (respctr[maxindx] < MaxRespCtr)
            respctr[maxindx]+ +;
        if (maxindx > 0)        {
            rm1indx = maxindx-1;
            respm1 = LPLrec[rm1indx].rslt > > 16;
            if (respm1 > = maxresp > > 1)       {
                avgrespn + = rm1indx+1 < < 1;
                    avgrctr+ +;
                if (respctr [rm1indx] < MaxRespCtr)
                respctr[rm1indx]+ +;
            }
```

```
        }
        if (maxindx < MaxResp) {
            rp1indx = maxindx+1;
            respp1 = LPLrec[rp1indx].rslt > > 16;
            if (respp1 > = maxresp > > 1)       {
                avgrespn + = rp1indx+1 < < 1;
                    avgrctr+ +;
                if (respctr[rp1indx] < MaxRespCtr)
                respctr[rp1indx]+ +;
            }
        }
        lstrpeak = maxrespn;
    }
    else
        if ((abs(maxindx - lstrindx) = = 1) || (maxrespn > =
            (lstrpeak + lstrpeak > > 1)))
            {
            if (respctr[lstrindx] > 0) {
                respctr[lstrindx]--;
                rctrtotal = respctr[lstrindx];
                avgrespn = lstrindx+1 < < 1; avgrctr =
                    1;
            }
            if (lstrindx > 0)       {
                rm1indx = lstrindx-1;
                if (respctr[rm1indx] > 0)       {
                respctr[rm1indx]--;
                avgrespn + = rm1indx+1 < < 1;
                    avgrctr+ +;
                rctrtotal + = respctr[rm1indx];       }
            }
            if (lstrindx < MaxResp)       {
                rp1indx = lstrindx+1;
                if (respctr[rp1indx] > 0)       {
                respctr[rp1indx]--;
                avgrespn + = rp1indx+1 < < 1;
                    avgrctr+ +;
                rctrtotal + = respctr[rp1indx];       }
            }
            if (rctrtotal = = 0) {
                lstrindx = maxindx;
                lstrpeak = maxrespn;}
        }
    if (avgrespn > 0)
        avgrespn = avgrespn/avgrctr;
    if (DetResp = = 0)
        LPRrec.rslt = (long) avgrespn < < 17;
    LPRrec.x0 = avgrespn < < 1;
    pLPrec = &LPRrec;
    dlpf(pLPrec);
    DetResp = LPRrec.rslt > > 16;
    }
else {
    if ((DetStat & 0xF000) != 0x1000) {
        for (i=0;i<MaxFLChan;i+ +)
            respctr[i] = 0;
        DetResp = 0;
        lstrindx = maxindx; }
}
```

In regards to the above exemplary code, the variable "DetStat" is representative of the detection status, wherein the detection status is checked to see if a respiration flag is set in a top or first level decision step or if statement. If it determined that the respiration flag is set, then the exemplary code determines if a newly detected peak respiration frequency equals the previous peak respiration frequency in a second level if statement. If it is determined that the newly detected peak respiration frequency equals the previous peak respiration frequency, then the frequency bin index associated with the peak respiration frequency is added to the "avgrespn" value, and the average respiration rate counter (avgrctr) is incremented. Typically, the "avgrespn" variable is representative of an average respiration rate, and will include the peak frequency, as well as the lower and/or upper adjacent frequency bin.

It is also determined in a third level if statement, if the respiration rate counter for the peak frequency bin (respctr [maxindx]) is less than a maximum respiration rate counter (MaxRespCtr) value. If it is determined that the respiration rate counter for the peak frequency bin (respctr[maxindx]) is less than the maximum respiration rate counter (MaxRespCtr) value, then the peak frequency respiration counter (respctr[maxindx]) is incremented. It is also determined if the peak frequency is not a frequency that corresponds to the lowest frequency bin in another third level if statement. If it is determined that the peak frequency is not a frequency that corresponds to the lowest frequency bin, then the next lowest frequency bin index is assigned to the "rm 1 indx" variable, and it is determined if the amplitude of the lower frequency bin is greater than or equal to half the amplitude of the peak frequency bin in a fourth level if statement. Typically, the "rm 1 indx" variable is representative of the first lower frequency bin adjacent to the peak frequency bin. If it is determined that the amplitude of the lower frequency bin is greater than or equal to half the amplitude of the peak frequency bin, then the lower frequency bin index is also added to the "avgrespn" variable value (average respiration rate), the average respiration rate counter (avgrctr) is incremented, and it is determined if the respiration counter (respctr) value is less than a maximum respiration rate counter (MaxRespCtr) value in a fifth level if statement. If it is determined that the respiration rate counter (respctr) value is less than the maximum respiration rate counter (MaxRespCtr) value, then the lower adjacent respiration counter (respctr[rm 1 indx]) is incremented.

Additionally, if it is determined that the newly detected peak respiration frequency equals the previous peak respiration frequency then it is determined if the peak frequency is not the highest frequency bin in yet another third level if statement. If it is determined that the peak frequency is not the highest frequency bin, then the next highest frequency bin index is assigned to the "rp 1 indx" variable, and it is determined if the amplitude of the higher frequency bin is greater than or equal to half the amplitude of the peak frequency bin in another fourth level if statement. Typically, the "rp 1 indx" variable is representative of the higher adjacent frequency bin. If it is determined that the amplitude of the higher frequency bin is greater than or equal to half of the amplitude of the peak frequency bin, then the higher frequency bin index is added to the "avgrespn" variable value, the average respiration rate counter (avgrctr) is incremented, and it is determined at the respiration counter (respctr [rp 1 ndx]) value is less than the maximum respiration rate counter (MaxRespCtr) value in another fifth level if statement. If it is determined that the respiration counter (respctr[rp 1 indx]) value is less than the maximum respiration rate counter (MaxRespCtr) value, then the lower adjacent respiration counter (respctr[rp 1 indx]) is incremented.

However, if it is determined that the newly detected peak respiration frequency does not equal the previous peak respiration frequency, then the above counters are all decremented if the counters are above their minimum counter values (second level else statement). In the event that the above counters equal the minimum values and it is determined that the average respiration rate value (avgrespn) is greater than zero, then the previous peak frequency is changed to the newly detected peak frequency. Thus, the counters related to the previous peak frequency are decremented to zero before a newly detected peak frequency is recognized as the new peak frequency. If it is determined that the average respiration rate value (avgrespn) is greater than zero, then the average respiration rate (avgrespn) is set to equal a value of the average respiration rate divided by the average respiration rate counter value (avgrespn/avgrctr). The determined value (avgrespn/avgrctr) is representative of a detected respiration rate reference valve, and is low pass filtered to provide smooth transitions from value to value and assigned to a detected respiration rate value represented by the variable "DetResp."

However, if it is determined that the respiration flag is not set, then the above counters are set to their minimum values and the output respiration value is set to zero (first level else statement).

Figure 3A:
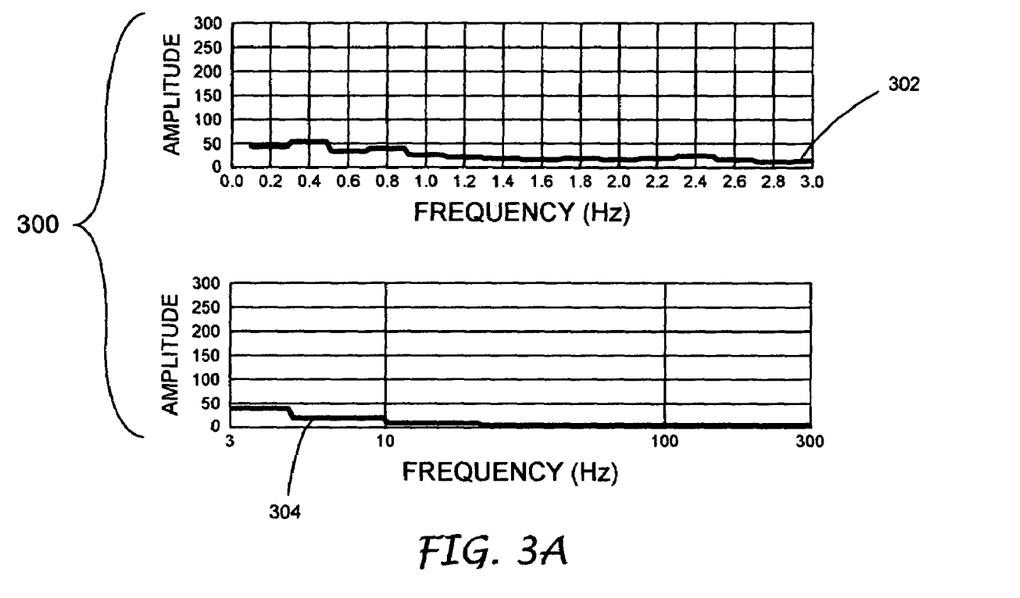
FIGS. 3A-3C are exemplary screen dumps presenting graphs illustrating exemplary respiration rates and body movements associated with a predetermined volume.
Figure 3B:
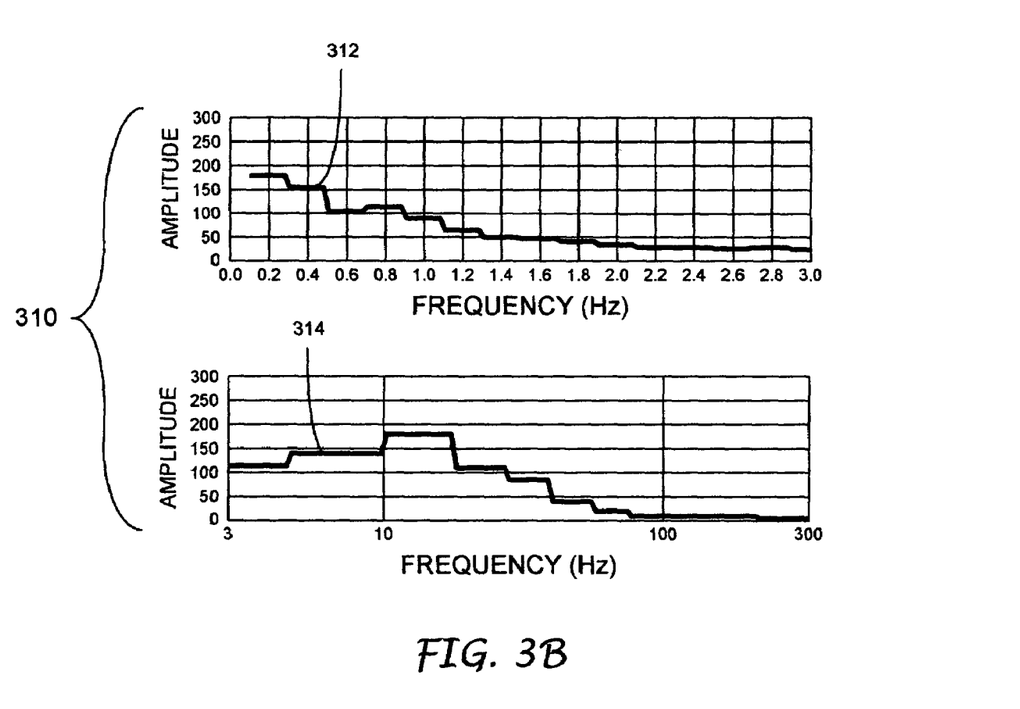
Figure 3C:
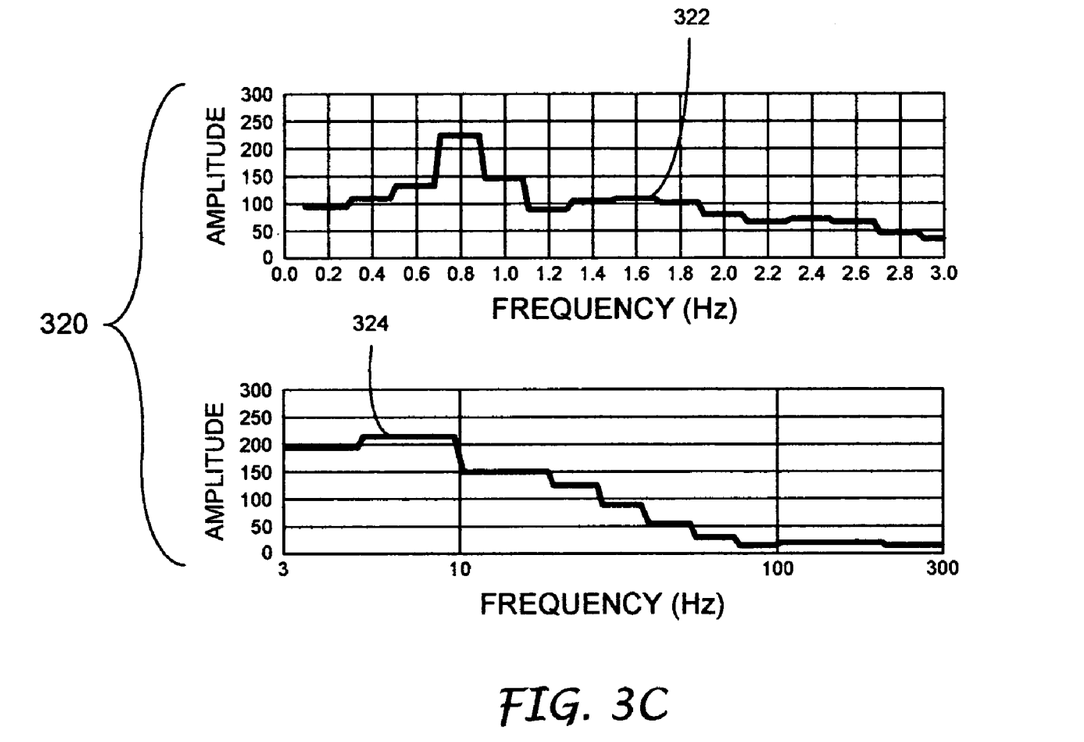

FIGS. 3A-3C depict exemplary screen dumps 300, 310 and 320 that depict exemplary data utilized by the ultrasonic sensing system 100. With specific reference to FIG. 3A, the screen dump 300 includes a respiration rate curve 302 and body movement curve 304. The curve 302 depicts the amplitude of frequencies located between 0 and 3 Hertz and indicate a detected respiration rate of zero for a predetermined volume. The curve 304 depicts detection of body movement between the frequency range of 3 to 300 Hertz and indicates that an occupant is not detected within the predetermined volume.

With reference to FIG. 3B, the screen dump 310 includes curves 312 and 314. The curve 312 is a respiration rate curve and provides an indication that an average respiration rate of approximately 0.3 Hertz has been detected. The curve 314 indicates that body movement has been detected and, thus, an occupant is present within a predetermined volume. The exemplary screen dump 320 of FIG. 3C includes curves 322 and 324. The curve 322 is a respiration rate curve and provides an indication that a respiration rate of approximately 0.5 Hertz has been detected and that a respiration rate change to 0.8 Hertz is occurring. The curve 324 indicates that body movement within the predetermined volume has been detected.

Accordingly, an ultrasonic sensing system has been described herein that is capable of acquiring, locking and tracking the respiration of an individual located within a predetermined volume, such as an automobile passenger compartment. Such a feature is particularly attractively combined with other sensor data, such as temperature and humidity, as it allows the ultrasonic sensing system to identify at-risk situations in an automobile passenger compartment or other enclosed areas and, thus, provide a warning such that a potentially tragic situation can be avoided.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A method for monitoring a respiration rate of an occupant of a predetermined volume, comprising the steps of:
    analyzing frequency component amplitudes of a received ultrasonic signal to determine a frequency content of the received ultrasonic signal, wherein the received ultrasonic signal is a composite signal that provides an indication of a respiration rate of an occupant present within a predetermined volume;
    determining whether a current frequency band having a peak amplitude is the same as a previous frequency band having a peak amplitude;

incrementing a current frequency band counter when the current frequency band is the same as the previous frequency band; and decrementing a previous frequency band counter when the current frequency band is not the same as the previous frequency band and the amplitude of the current frequency band is a predetermined amount greater than the amplitude of the previous frequency band.

2. The method of claim 1, wherein the previous frequency band counter is also decremented when the current frequency band is not the same as the previous frequency band and the current frequency band corresponds to a frequency band that is adjacent to the previous frequency band.

3. The method of claim 1, wherein the current frequency band counter and the previous frequency band counter are not altered unless the frequency component amplitudes of the received ultrasonic signal indicate a detected frequency band and the presence of the occupant in the predetermined volume.

4. The method of claim 1, wherein the current frequency band counter is only incremented if a value of the current frequency band counter is less than a predetermined maximum counter value and the current frequency band is the same as the previous frequency band.

5. The method of claim 2, wherein the previous frequency band counter is only decremented if a value of the previous frequency band counter is more than a predetermined minimum counter value.

6. The method of claim 1, further comprising the steps of:
determining whether amplitudes associated with frequency bands adjacent the current frequency band are within a predetermined value of an amplitude of the current frequency band;
incrementing an adjacent lower frequency band counter when the amplitude of the adjacent lower frequency band is within the predetermined value of the amplitude of the current frequency band;
incrementing an adjacent upper frequency band counter when the amplitude of the adjacent upper frequency band is within the predetermined value of the amplitude of the current frequency band; and
determining an average frequency band based on values of the adjacent lower frequency band counter, the adjacent upper frequency band counter, and the current frequency band counter.

7. The method of claim 6, wherein the adjacent lower frequency band counter is only incremented if a value of the adjacent lower frequency band counter is less than a predetermined maximum counter value.

8. The method of claim 7, wherein the adjacent upper frequency band counter is only incremented if a value of the adjacent upper frequency band counter is less than the predetermined maximum counter value.

9. The method of claim 8, wherein the counters are cleared when the frequency component amplitudes of the received ultrasonic signal indicate that there are no occupants present in the predetermined volume or the occupant does not have a respiration rate.

10. The method of claim 1, wherein the frequency content is between 0 and 3 Hertz.

11. An ultrasonic sensing system, comprising:
an ultrasonic transmitter positioned to transmit an ultrasonic signal into a predetermined volume;
an ultrasonic receiver positioned to receive a composite signal from the predetermined volume;
a processor coupled to the transmitter and the receiver; and
a memory subsystem coupled to the processor, the memory subsystem storing code that when executed by the processor instructs the processor to perform the steps of:
analyzing frequency component amplitudes of a received ultrasonic signal to determine a frequency content of the received ultrasonic signal, wherein the received ultrasonic signal is a composite signal that provides an indication of a respiration rate of an occupant present within a predetermined volume;
determining whether a current frequency band having a peak amplitude is the same as a previous frequency band having a peak amplitude;
incrementing a current frequency band counter when the current frequency band is the same as the previous frequency band; and
decrementing a previous frequency band counter when the current frequency band is not the same as the previous frequency band and the amplitude of the current frequency band is a predetermined amount greater than the amplitude of the previous frequency band.

12. The system of claim 11, wherein the previous frequency band counter is also decremented when the current frequency band is not the same as the previous frequency band and the current frequency band corresponds to a frequency band that is adjacent to the previous frequency band.

13. The system of claim 11, wherein the current frequency band counter and the previous frequency band counter are not altered unless the frequency component amplitudes of the received ultrasonic signal indicate a detected frequency band and the presence of the occupant in the predetermined volume.

14. The system of claim 11, wherein the current frequency band counter is only incremented if a value of the current frequency band counter is less than a predetermined maximum counter value and the current frequency band is the same as the previous frequency band.

15. The system of claim 12, wherein the previous peak respiration frequency band counter is only decremented if a value of the previous frequency band counter is more than a predetermined minimum counter value.

16. The system of claim 11, the memory subsystem storing additional code for instructing the processor to perform the additional steps of:
determining whether amplitudes associated with frequency bands adjacent the current frequency band are within a predetermined value of the amplitude of the current frequency band;
incrementing an adjacent lower frequency band counter when the amplitude of the adjacent lower frequency band is within the predetermined value of the amplitude of the current frequency band;
incrementing an adjacent upper frequency band counter when the amplitude of the adjacent upper frequency band is within the predetermined value of the amplitude of the current frequency band; and
determining an average frequency band based on values of the adjacent lower frequency band counter, the adjacent upper frequency band counter, and the current frequency band counter.

17. The system of claim 16, wherein the adjacent lower frequency band counter is only incremented if a value of the adjacent lower frequency band counter is less than a predetermined maximum counter value.

18. The system of claim 17, wherein the adjacent upper frequency band counter is only incremented if a value of the adjacent upper frequency band counter is less than the predetermined maximum counter value.

19. The system of claim 18, wherein the counters are cleared when the frequency component amplitudes of the received ultrasonic signal indicate that there are no occupants present in the predetermined volume or the occupant does not have a respiration rate.

20. The system of claim 11, wherein the frequency content is between 0 and 300 Hertz.

21. An ultrasonic sensing system, comprising:
   an ultrasonic transmitter positioned to transmit an ultrasonic signal into a predetermined volume;
   an ultrasonic receiver positioned to receive a composite signal from the predetermined volume;
   a processor coupled to the transmitter and the receiver; and
   a memory subsystem coupled to the processor, the memory subsystem storing code that when executed by the processor instructs the processor to perform the steps of:
      analyzing frequency component amplitudes of a received ultrasonic signal to determine a frequency content of the received ultrasonic signal, wherein the received ultrasonic signal is a composite signal that provides an indication of a respiration rate of an occupant present within a predetermined volume;
      determining whether a current frequency band having a peak amplitude is the same as a previous frequency band having a peak amplitude;
      incrementing a current frequency band counter when the current frequency band is the same as the previous frequency band; and
      decrementing a previous frequency band counter when the current frequency band is not the same as the previous frequency band and the current frequency band corresponds to a frequency band that is adjacent to the previous frequency band.

22. The system of claim 21, wherein the previous frequency band counter is also decremented when the current frequency band is not the same as the previous frequency band and the amplitude of the current frequency band is a predetermined amount greater than the amplitude of the previous frequency band.

23. The system of claim 21, wherein the current frequency band counter and the previous frequency band counter are not altered unless the frequency component amplitudes of the received ultrasonic signal indicate a detected respiration rate and the presence of the occupant in the predetermined volume.

24. The system of claim 21, wherein the current frequency band counter is only incremented if a value of the current frequency band counter is less than a predetermined maximum counter value and the current frequency band is the same as the previous frequency band.

25. The system of claim 22, wherein the previous frequency band counter is only decremented if a value of the previous frequency band counter is more than a predetermined minimum counter value.

26. The system of claim 21, the memory subsystem storing additional code for instructing the processor to perform the additional steps of:
   determining whether amplitudes associated with frequency bands adjacent the current frequency band are within a predetermined value of the amplitude of the current frequency band;
   incrementing an adjacent lower frequency band counter when the amplitude of the adjacent lower frequency band is within the predetermined value of the amplitude of the current frequency band;
   incrementing an adjacent upper frequency band counter when the amplitude of the adjacent upper frequency band is within the predetermined value of the amplitude of the current frequency band; and
   determining an average frequency band based on values of the adjacent lower frequency band counter, the adjacent upper frequency band counter, and the current frequency band counter.

27. The system of claim 26, wherein the adjacent lower frequency band counter is only incremented if a value of the adjacent lower frequency band counter is less than a predetermined maximum counter value.

28. The system of claim 27, wherein the adjacent upper frequency band counter is only incremented if a value of the adjacent upper frequency band counter is less than the predetermined maximum counter value.

29. The system of claim 28, wherein the counters are cleared when the frequency component amplitudes of the received ultrasonic signal indicate that there are no occupants present in the predetermined volume or the occupant does not have a respiration rate.

30. The system of claim 21, wherein the frequency content is between 0 and 3 Hertz.

* * * * *